United States Patent [19]

Young

[11] 4,162,155

[45] Jul. 24, 1979

[54] COMPOSITIONS

[75] Inventor: David W. Young, Homewood, Ill.

[73] Assignee: Howard Hall & Company, Cos Cob, Conn.

[21] Appl. No.: 772,139

[22] Filed: Feb. 25, 1977

Related U.S. Application Data

[63] Continuation of Ser. No. 568,919, Apr. 17, 1975, abandoned.

[51] Int. Cl.$^2$ .......................... A01N 9/02; A01N 9/24
[52] U.S. Cl. ............................................ 71/110; 71/93; 71/121; 71/124; 252/403; 424/190; 424/200
[58] Field of Search .......................... 252/403; 71/110; 260/562 A

[56] References Cited

U.S. PATENT DOCUMENTS

| | | | |
|---|---|---|---|
| 992,265 | 5/1911 | Schlaugk | 252/403 X |
| 1,634,054 | 6/1927 | Sommerville | 252/403 X |
| 2,151,651 | 3/1939 | Christmann | 252/403 X |
| 2,654,722 | 10/1953 | Young | 252/403 X |
| 2,730,500 | 1/1955 | Young et al. | 252/403 X |
| 2,824,838 | 2/1958 | Young et al. | 252/403 X |
| 2,901,502 | 8/1959 | Young et al. | 260/562 A X |
| 3,748,358 | 7/1973 | Baron | 260/562 A |
| 3,789,008 | 1/1974 | Young | 423/317 X |

*Primary Examiner*—Joseph Paul Brust
*Attorney, Agent, or Firm*—Bernard & Brown

[57] ABSTRACT

Agriculturally-active aqueous compositions containing an agriculturally-active organic substance and water are stabilized by the addition to the system of a minor amount of N-acetyl-p-aminophenol. The N-acetyl-p-aminophenol is relatively non-toxic and is degradable, thereby making it particularly attractive for agricultural use in view of its high degree of effectiveness as a stabilizer. Advantageous agriculturally-active organic substances are the compounds having carbon to carbon unsaturation, particularly those having aliphatic unsaturation.

6 Claims, No Drawings

COMPOSITIONS

This is a continuation of application Ser. No. 568,919, filed Apr. 17, 1975, now abandoned.

This invention relates to the stabilization of agriculturally-active organic substances in aqueous systems, which organic substances tend to deteriorate in storage or in use due to, for instance, oxidation.

Inorganic insecticide agents have been employed in agricultural application for insecticides, miticides, herbicides, and the like. Lead arsenanate is a common example of an inorganic insecticide. These agents can readily be used in agricultural applications since they are easily suspended in water. Moreover, the inorganic agents are generally insensitive to undue oxidation and deterioration and thus are inherently persistent. However, inorganic agents have been found objectionable in that they often are toxic to higher animal life before, during, and after their use. The stability against deterioration which such agents inherently provide may be disadvantageous in that the potentially poisonous residue of the agents will remain for long periods of time.

To overcome such difficulties with inorganic insecticides and the like for agricultural use, organic materials have been adopted. Many agriculturally-active substances such as insecticides, miticides, and herbicides exhibit low toxicity to higher animal life and are capable of deterioration to relatively innocuous components. In some instances, the stability of the organic material is so limited that frequent reapplications of the organic material are required to maintain the desired activity. Applications of organic agricultural materials have been as dusts and oil or water based forms or sprays. Many of the organic agricultural materials are oil soluble; however, the use of oil sprays or foams in agricultural applications may provide enviromental problems as well as potentially exhaust valuable petroleum supplies.

The effects of agricultural materials, due to their use, may affect surrounding areas. For instance, an insecticide may be carried by the wind from the area in which it is being applied to neighboring areas. Rain may wash the insecticide away from the fields to which it is applied and to rivers and the like. Due to the high volumes of organic agricultural materials employed throughout the world, the stability, rate of deterioration, and activity of such organic agricultural materials and formulations thereof are of prime environmental interest.

It has been proposed to employ stabilizers with insecticides to retard the deterioration of the insecticide caused by exposure to light and air or oxygen. For instance, Christmann et al. in U.S. Pat. No. 2,151,651 disclose the use of aminophenol as a stabilizer for rotenone in organic solvent or in dust form. Stabilizers such as aminophenol, however, may be disadvantageous for widespread use in view of toxicity to higher forms of life. For instance, p-aminophenol is moderately toxic and is a skin irritant. Acyl-para-aminophenols have been suggested as antioxidant for solid organic materials in U.S. Pat. No. 2,654,722. The acyl substituent in these antioxidants has at least three carbons and antioxidant is highly insoluble in water.

A stabilizer for agriculturally-active organic substances which are applied in an aqueous medium should be compatible with the organic material and water. The stabilizer should be effective to retard deterioration of the organic material, but the activity of the organic agricultural material should not be unduly extended. The stabilizer should not, however, deteriorate from the effectiveness of the agriculturally-active organic substance and it should not itself present a hazard to high forms of life. Preferably, the stabilizer should be capable of being deteriorated.

In accordance with this invention agriculturally-active organic substances in aqueous systems are stabilized by the addition to the system of a minor, stabilizing amount of N-acetyl-p-aminophenol. The N-acetyl-p-aminophenol has limited solubility in water and is also compatible with organic agricultural materials, and thus can be an effective stabilizer in the aqueous phase and the organic phase, if separate phases exist. Moreover, frequently clays are employed in agricultural formulations, and these clays often have an acidic or basic effect on water. This effect often leads to accelerated deterioration of an agriculturally-active organic substance. N-acetyl-p-aminophenol is an effective stabilizer in such clay-containing formulations. Also, N-acetyl-p-aminophenol reduces the rate of sublimation of agriculturally-active organic substances, thereby increasing the duration of the desired agricultural activity. N-acetyl-p-aminophenol is relatively non-toxic and is degradable, thereby making it particularly attractive for agricultural use in view of its high degree of effectiveness as a stabilizer.

The agriculturally-active organic substances of this invention includes hydrocarbon-containing materials which have, for instance, insecticidal, miticidal, herbicidal, fungicidal, nematicidal, plant growth-controlling regulation, e.g. plant hormones, or the like, properties which are of particular benefit in agricultural applications, even those which are relatively unconfined and are exposed to the environment. The agriculturally-active organic substance is used in an amount effective to provide the desired activity and is capable of being dispersed in water for a time at least sufficient to enable its application. By dispersion, it is meant that the organic substance is soluble in water or is capable of otherwise being dispersed in the medium. In an aspect of the invention, the agriculturally-active organic substance is soluble in water.

Exemplary of agriculturally-active organic substances which may be employed in this invention are the nicotinoidpyrethroids, rotenoids, sabadilla, ryania, dinitroaryls of one or two aryl rings (dinitrophenols), organothiccyanates, chloro-(chlorophenyl)ethanes, chlorinated hexanes, chlorinated terpenes, cyclodines, organophosphorous compounds, for instance phosphates, phosphites, phosphonates, phosphorothioates, phosphorodithioates, and the like, triazines, amidines, and cabamates. Advantageous agriculturally-active organic substances are the compounds containing carbon to carbon unsaturation, particularly those compounds in which the carbon to carbon unsaturation is aliphatic unsaturation, for instance, the pyrethroids, rotenoids, the vinyl phosphates including those described in U.S. Pats. Nos. 2,744,128; 2,788,358; 2,865,944; 2,867,646; 2,891,887; 2,894,014; 2,894,018; 2,895,982; 2,898,341; 2,913,367; 2,956,073; and 3,097,128; the esters of isooctenyl alcohol such as are disclosed in U.S. Pat. No. 3,005,016, and copolymer esters of styrenes and maleic anhydride as are disclosed in U.S. Pat. No. 3,697,250.

Some agriculturally-active organic substances having aliphatic unsaturation are isooctenyl 2,4-dichlorophenoxy acetate, 2-methyl-2-(methylthio)propionaldehyde 0-(methylcarbanoyl)oxime, 0, 0-dimethyl 0-(1-methyl-2-(1-phenylcarbethoxy)vinyl) phosphate, 3-

(dimethoxyphosphinyloxy)-N,N-dimethylcrotonamide, 4,6-dinitro-o-caprylphenyl crotonate, 4-chloro-3-butynyl m-chlorocarbanilate, N,N-dialkyl-2-chloroacetamide, rotenone, dimethyl 2-carbomethoxy-1-methylvinyl phosphate, dimethyl 2,2-dichlorovinyl phosphate, dimethyl 2-benzyloxycarbonyl-1-methylvinyl phosphate, dimethyl 2-phenyloxycarbonyl-1-methylvinyl phosphate, dimethyl 2-(alphamethylbenzyloxycarbonyl)-1-methylvinyl phosphate, 2-carbomethoxy-1-methylvinyl methyl p-nitrophenyl phosphate, 2-(2-acetoxyethoxycarbonyl)-1-methylvinyl dimethyl phosphate, 2-(2benzoyloxyethoxycarbonyl)-1-methylvinyl dimethyl phosphate, 2-(2-methoxyethoxycarbonyl)-1-methylvinyl dimethyl phosphate, 2-carbethoxy-1-methylvinyl ethyl 2-methoxyethyl phosphate, methyl 2-carbethoxy-1-methylvinyl phenylphosphonate, ethyl 2-methoxycarbonyl-1-methylvinyl dimethylaminophenylphosphonate, 2-(2-carbethoxyvinyloxy)-4-methyl-2-oxy-1,3,2-dioxaphospholane, 2-(m-nitrobenzyloxycarbonyl)-1-methylvinyl dimethyl phosphate, 2-(p-nitrobenzyloxycarbonyl)-1-methylvinyl dimethyl phosphate, dimethyl 1-methyl-2-(p-tolyloxycarbonyl)vinyl phosphate, dimethyl 2-phenethyloxycarbonyl-1-methylvinyl phosphate, 2-(p-methoxybenzyloxycarbonyl)-1-methylvinyl dimethyl phosphate, 2-phenoxyethoxycarbonyl-1-methylvinyl dimethyl phosphate, 2-(p-chlorophenoxycarbonyl)-1-methylvinyl dimethyl phosphate, 2-(p-chlorobenzyloxycarbonyl)-1-methylvinyl dimethyl phosphate, diethyl 2-carboethoxy-1-methylvinyl phosphate, dimethyl 2-carbomethoxy-2-phenylvinyl phosphate, diethyl 2-carboethoxy-1-cyclopenten-1-yl phosphate, diethyl 2-carbethoxy-2-chlorovinyl phosphate, diethyl 1-ethoxy-2-carbethoxy-2-chlorovinyl phosphate, 2-chloro-2-carbethoxy-1-methylvinyl dimethyl phosphate, 2-benzyloxycarbonyl-1-methylvinyl methyl phenyl phosphate, 2-carbethoxyvinyl dimethyl phosphate, 2-chlorovinyl dimethyl phosphate, 0,0-diethyl 0-2-(ethylthio)-carbonyl-1-methylvinyl phosphorothioate, 0-(p-chlorophenylsulfoxylethyl) 0-ethyl 0-1-methyl-2-carbethoxyvinyl phosphate, 2-chloro-2-(methoxycarbonyl)-1-methylvinyl dimethyl phosphate, diethyl 2-carbethoxy-1-cyclophentenyl-yl thionophosphate, 2-chloro-2-acetyl-1-methylvinyl diethyl phosphate, 2,2-dichlorovinyl di-sec-butyl phosphate, 2,2-dichlorovinyl ethyl phenylphosphonate, 2,2-dibromovinyl dimethyl phosphate, 2,2-dichloro-1-phenylvinyl dimethyl phosphate, 2-chloro-1-phenylvinyl diethyl phosphate, 2-chloro-2-carbethoxy-1-methylvinyl diethyl phosphate, 2,2-dichlorovinyl ethyl 1,2-dichloropropyl phosphate, the 2-halo-4,6-dialkylamino-sstriazines (e.g., 2-chloro-4-ethylamino-6-isopropylamino-s-triazine and 2-chloro-4,6-bis-(ethylamino)-s-triazine, N,(cyclopropylmethyl)-α,α,α-trifluoro-2,6-dinitro-N-propyl-p-toluidine, 0,0-dimethyl phosphorodithiozole, 5-ester with 4-(mercaptomethyl)-2-methoxy-Δ²-1,3,4-thiadiazolin-5-one, N'-(4-chloro-o-tolyl)-N,N-dimethylformamide, p-nitrophenyl-2-nitro-4-(trifluoromethyl)-phenyl ether, 0,0-diethyl-0-(2-isopropyl-6-methyl-4-pyrimidinyl) phosphorothioate, and the like.

The N-acetyl-p-aminophenol is provided in a minor amount based on the weight of the agriculturally-active organic substance which is sufficient to stabilize, or retard the deterioration of, the agriculturally-active organic substance at least for a suitable time for the agriculturally-active organic substance to be effective. The amount of N-acetyl-p-aminophenol which is employed in accordance with this invention may depend on the desired period of activity of the agriculturally-active organic substance and the rate of deterioration of the agriculturally-active organic substance. Thus, increased amounts of N-acetyl-p-aminophenol may be employed when an increased active life time of the agricultural material is desired. The period of activity may be adjusted to reduce the need for repeated, periodic applications of the agricultural material, but avoid an unnecessary, prolonged active life. Frequently, the N-acetyl-p-aminophenol will be provided in an amount of at least about 0.01 percent, preferably at least about 0.03 percent, by weight based on the weight of the agriculturally-active organic substance. Concentrations of about 0.15 percent or more of N-acetyl-p-aminophenol based on the agriculturally-active organic substance are frequently employed in accordance with this invention. At concentrations in excess of about 5 percent by weight based on the weight of the agriculturally-active substance, little benefit in increased stability is generally observed, and often concentration of N-acetyl-p-aminophenol is up to about 1 percent. The N-acetyl-p-aminophenol, due to its ability to deteriorate under atmospheric exposure, its relative non-toxicity, and the low concentrations which can be effectively employed, is not unduly deleterious to the environment even in high volume agricultural applications.

The presence of N-acetyl-para-aminophenol usually does not affect the manner by which the organic agricultural material may be formulated to provide an aqueous mixture which is capable of being distributed in a convenient manner such as by a spray or foam. The N-acetyl-para-aminophenol is preferably uniformly admixed in the aqueous agricultural material mixture. The N-acetyl-para-aminophenol may be added at the time of formultion of the final mixture for application, or it may be intimately premixed with the agriculturally-active organic substance which may be in solid or liquid form prior to formulation the aqueous composition of this invention.

It is often convenient to provide an aqueous agriculturally-active or treating composition in which the volume of the product can easily be handled, particularly when the formulation must be transported for its application. On the other hand, this invention is applicable to systems wherein the agriculturally-active organic substance is at high dilution, for instance, when it is distributed through an irrigation system. Preferably, the active organic substance may be a minor amount of the aqueous composition sufficient to be effective when applied. N-Acetyl-para-aminophenol has been found to inhibit rusting of ferrous metals when they are contacted with an aqueous solution of the N-acetyl-para-aminophenol as would occur, for example, when such solutions are pumped through iron-containing pipes which would otherwise rust. Accordingly, the aqueous agriculturally-active composition of this invention exhibits such anti-rusting properties. The concentration of the agriculturally-active organic substance in the compositions of this invention may be very small, say about 100 parts per million by weight or less, or it can be present in major amount say on the order of about 50 or 60 or more percent by weight of the total composition. Frequently, water is present in an amount sufficient to form a continuous phase in the composition of this invention, and is present in a major amount sufficient to provide a carrier for the agriculturally-active organic substance. The formulation may be shipped in concentrated form, say having up to about 90 or 95 or more percent agriculturally-active organic substance and diluted prior to use.

The mixture may contain such emulsifiers or suspension agents as are desired to provide a suitably stable dispersion of the agriculturally-active organic substance. The emulsifier or suspension agent may be present in a minor amount based on the weight of the agriculturally-active organic substance which is sufficient to maintain adequate dispersion of the agriculturally-active organic substance in the composition for at least a sufficient time for its application. Frequently, the emulsifier or suspension agent is present in an amount of about 0.01 to 5 or more percent by weight of the active organic substance. Generally no surface active agent is required to disperse the N-acetyl-p-aminophenol in the aqueous solution.

Various non-ionic, cationic anionic, amphoteric or amphelyic surfactants which may find application in the aqueous agricultural material mixtures include, for example, block copolymers of ethylene oxide and propylene oxide (such as the commercially available material Pluronic L61), alkylarylethylenoxide condensates, e.g., nonyl phenol polyethyleneoxide (such as the commercially available material Lissapol N), alkali metal salts of stearic acid, polyethyleneoxide esters of stearic acid (as, for example, the commercially available material Ethofat 60/15), polyoxyethylene sorbitan monolaurate (commercially available as Tween-20), polyoxyethylene sorbitan monoleate (commercially available as Tween-80), mixtures of alkyl aryl sulfonates and polyoxyethylene sorbitan esters of fatty acids (such as Altox G-2018), alkylamino carboxylic acids, alkali metal alkyl sulfates, alkyl trialkylaminonium halides, etc. Silicone surfactants may also find application in agriculturally-active compositions. More than simply effecting a dispersion, suspension or emulsion of the selected chemicals in the aqueous vehicle, however, it is further required of a suitable surface-active agent that, for instance, the surfactant be non-deleterious to the plants to be treated, that it leave little or no visible deposit on the vegetation which remains to harvest and, just as important, that it be economical, for example, that it provide an effective dispersion when present in very small concentrations in the aqueous compositions. The surfactant may also assist in providing a thin film of the active organic substance on leaves, fruit, and the like.

Humectants may also be employed in aqueous agricultural material compositions to improve penetration of the agriculturally-active substance into plant leaves or the ground by retarding the rate of drying of the spray deposit, thereby increasing the penetration time. Often low molecular weight glycols, for instance glycerol, ethylene glycol, propylene glycol and the like may be employed as humectants, although more complex compounds such as Carbowax, sucrose, molasses, and polypropylene diol are also useful. Other additives which may be employed in the aqueous composition include, for instance, antidrift agents, thickeners, deposit builders, particulating agents, spray gell agents, and the like. Dimethyl sulfoxide may also be employed in herbicide or pesticide compositions for which their uptake by the intended host is enhanced by the presence of dimethyl sulfoxide.

The agriculturally-active or treating composition may also contain a minor amount of a finely-divided solid material, for instance, up to about 600 microns in diameter, preferably about 0.5 to 500 microns in diameter, which may serve as a substitute for the agriculturally-active organic material or otherwise assist in the application of the agriculturally-active organic material with safety to the applicator, plants, and animals. When the composition is to be applied by spraying, the finely-divided solid material should be sufficiently small that undue clogging of spray nozzles does not occur. The finely-divided solid material may, for instance, be provided in an amount of about 0.001 to 20 percent by weight of the total composition. Typical finely-divided solid materials for agricultural use include clay, bentonite, diatomacious earth, attapulgite, silicon oxides, lime, gypsum, talc, and the like.

The following examples are provided to further illustrate the invention. All parts and percentages are by weight unless otherwise noted.

EXAMPLE I

Aqueous mixtures of AAtrex ® weed control composition (AAtrex is held by Ciba-Geigy Corporation and comprises atrazine, which is 2-chloro-4-ethylamino-6-isopropylamino-5-triazine, and exhibits herbicidal properties) and varying amounts of N-acetyl-p-aminophenol are prepared by admixing the constituents in a glass flask and agitating at about 20° to 24° C. for three hours. Each mixture is added to a clean Volck type spray gun and sprayed on 100 milliliter etched round bottom glass flask which is slowly revolved during the transfer. The flasks are maintained at about 25° C. in a rubber and plastic type, air circulating, aging oven. The weight of each flask is recorded before and after the aging tests. The results are provided in Table I.

| Composition | Total Spraying Time | Active Organic AAtrex 80W Coating Deposit mg./sq. in. | | Percentage Active AAtrex 80W loss from surface coating |
|---|---|---|---|---|
| | | After ½ hr. | After 7 days | |
| AAtrex 80W, 2 lbs. per 100 gal. water | 15 sec. | 0.190 | 0.013 | 45 |
| AAtrex 80W, 2 lbs. per 100 gal. water, plus 0.1% N-acetyl-p-aminophenol | 15 sec. | 0.187 | 0.094 | 50 |
| AAtrex 80W, 2 lbs. per 100 gals. water, plus 0.25% N-acetyl-p-aminophenol | 15 sec. | 0.240 | 0.156 | 35 |
| AAtrex 80W, 2 lbs. per 100 gal. water, plus 0.50% N-acetyl-p-aminophenol | 15 sec. | 0.175 | 0.112 | 36 |
| AAtrex 80W, 2 lbs. per 100 gal. water, plus 1.00% N-acetyl-p-aminophenol | 15 sec. | 0.244 | 0.163 | 33 |
| AAtrex 80W, 2 lbs. per 100 gal. water, plus 2.00% N-acetyl-p-aminophenol | 15 sec. | 0.201 | 0.140 | 31 |

The results indicate that N-acetyl-p-aminophenol stabilizes the agriculturally-active organic substance and decreases its evaporation or sublimation to the atmosphere. Similar results may be observed employing other agriculturally-active organic substances instead of atrazine.

The weight loss method of determining deterioration of AAtrex 80W in this example is compared with a gas chromator aphic analysis of the AAtrex 80W in the surface coating. The gas chromatographic analysis verifies that the weight change tests is a proper evaluation of the AAtrex 80W content in the coating.

EXAMPLE II

Various agriculturally-active organic substances are tested for oxidation stability in accordance with the method set forth as ASTM Method D 942-50. For each material there is conducted a run containing 0.25 weight percent N-acetyl-p-aminophenol based on weight of the agriculturally-active organic substances and a control. The active organic substance is in an amount of about 5 percent of the aqueous treating agent. The results are provided in Table II. The agricultural materials employed are Tolban $^{TM}$ 4E (N-(cyclopropylmethyl)-α, α, α-trifluoro-2,6-dinitro-N-propyl-p-toluidine, a herbicide obtainable from Ciba-Geigy Corporation); Surpacide ® 2E (0,0dimethyl phosphorodithioate, S-ester with 4-(mercapto methyl)-2-methoxy- $\Delta^2$-1,3,4-thiadiazolin-5-one, an insecticide available from Ciba-Geigy Corporation); Galecron ® 4E (N'-(4-chloro-o-tolyl)-N,N-dimethyl-formamidine, an acricide, ovicide and insecticide available from Ciba-Geigy Corporation); Preforan ® 3E (p-nitrophenyl-2-nitro-4-trifluoromethyl)phenyl ether, a herbicide available from Ciba-Geigy Corporation); Diazinon ® 4E (0,0-diethyl-0-(2-isopropyl-6-methyl-4-pyrimidinyl) phosphorothioate, an insecticide and nematicide available from Ciba-Geigy Corporation); Princep ® 80W (2-chloro-4,6-bis-(ethylamino)-s-triazine a herbicide available from Ciba-Geigy Corporation); and AAtrex 80W, hereabove defined.

TABLE II
TEST FOR OXIDATION STABILITY
*ASTM METHOD D 942-50

| Chemical In Test | Concentration Of N-Acetyl-p-Aminophenol | PSI Oxygen Absorbed |
|---|---|---|
| Tolban $^{TM}$ 4E | 0.25% | 15 |
| Tolban $^{TM}$ 4E | 0.00% | 35 |
| Supracide ® 2E | 0.25% | 8 |
| Supracide ® 2E | 0.00% | 22 |
| Galecron ® 4E | 0.25% | 5 |
| Galecron ® 4E | 0.00% | 18 |
| Preforan ® 3E | 0.25% | 18 |
| Preforan ® 3E | 0.00% | 17 |
| Diazinon ® 4E | 0.25% | 9 |
| Diazinon ® 4E | 0.00% | 44 |
| Princep ® 80W | 0.25% | 15 |
| Princep ® 80W | 0.00% | 14 |
| AAtrex ® 80W | 0.25% | 12 |
| AAtrex ® 80W | 0.00% | 31 |

*ASTM Test Modified as follows:
Temperature of Test Run: Change from 99° C. to 50°-54° C. Agitated Rocker Bomb Used.

EXAMPLE III

The vapor toxicity of a composition of the herbicide, isooctenyl ester of 2,4-dichlorophenoxyacetic acid, and N-acetyl-p-aminophenol is determined. Pregerminated cucumber seeds, a susceptible crop for use of the herbicide, are used as test specimens. The seeds are sealed in polyethylene bags containing sufficient moisture for normal growth and a predetermined quantity (about 3.36 grams) of the ester on filter paper. The test specimens are maintained at 70° to 80° F. for 72 hours and the root elongation determined at the end of this time. At effective-stabilizing concentrations of N-acetyl-p-aminophenol, no adverse effects on vapor-toxicity are observed, as compared to a herbicide composition containing the isooctenyl ester of 2,4-dichlorophenoxyacetic acid without N-acetyl-p-aminophenol.

Compositions containing about four ounces of isooctenyl ester of 2,4-dichlorophenoxyactic acid per gallon of water with effective-stabilizing concentrations of N-acetyl-p-aminophenol are applied in an amount of wet the weed or woody plant in a grass plot. The percent of weed kill is at least as good as a control not having the N-acetyl-p-aminopheonol.

For instance, with a concentration of 0.05 weight percent N-acetyl-p-aminophenol based on total weight of isooctenyl-2,4-dichlorophenoxy acetate, the average root lengths of the cucumber seeds are 37 millimeters whereas the average root lengths are 32 millimeters employing the isooctenyl-2,4-dichlorophenoxy acetate without the N-acetyl-p-aminophenol, and 55 millimeters for a control. The weed kill of isoocentyl-2,4-dichlorophenoxy acetate and 0.05 weight percent N-acetyl-p-aminophenol is 67 percent, whereas the weed kill with isooctenyl-2,4-dichlorophenoxy acetate without N-acetyl-p-aminophenol is 61 percent.

EXAMPLE IV

The procedure of Example II is essentially repeated except employing isooctenyl-2,4-dichlorophenoxyacetic acid (isooctenyl-2,4-dichlorophenoxy acetate) as the agriculturally-active organic substance. The composition exhibits good oxidation stability.

A composition containing isooctenyl-2,4-dichlorophenoxy acetate and N-acetyl-aminophenol exhibits excellent storage stability in comparison to a composition not containing the N-acetyl-p-aminophenol. The pressure of finely-divided clay in an aqueous composition also containing isooctenyl-2,4-dichlorophenoxy acetate and N-acetyl-p-aminophenol exhibits a better storage stability than a similar composition not containing N-acetyl-p-aminophenol.

What is claimed is:

1. An aqueous agriculturally-active composition comprising isooctenyl-2,4-dichlorophenoxy acetate; N-acetyl-p-aminophenol in an amount sufficient to stabilize isooctenyl-2,4-dichlorophenoxy acetate from deterioration; and water.

2. The aqueous agriculturally-active composition of claim 1 wherein the N-acetyl-p-aminophenol is in an amount of at least about 0.01 percent by weight based on the weight of the isooctenyl-2,4-dichlorophenoxy acetate.

3. The aqueous agriculturally-active composition of claim 2 wherein the N-acetyl-p-aminophenol is in an amount of about 0.01 to about 5 percent by weight based on the weight of the isooctenyl-2,4-dichlorophenoxy acetate.

4. The aqueous agriculturally-active composition of claim 1 wherein the isooctenyl-2,4-dichlorophenoxy acetate is present in an amount of up to about 90 percent by weight of the composition.

5. The aqueous agriculturally-active composition of claim 1 wherein water is provided as a carrier.

6. The aqueous agriculturally-active composition of claim 5 wherein water is in a continuous phase.

* * * * *